United States Patent
Pusch et al.

(10) Patent No.: US 7,731,759 B2
(45) Date of Patent: Jun. 8, 2010

(54) CONTROL OF A PASSIVE PROSTHETIC KNEE JOINT WITH ADJUSTABLE DAMPING

(75) Inventors: Martin Pusch, Duderstadt (DE); Sven Zarling, Duderstat (DE); Herman Boiten, Gottingen (DE)

(73) Assignee: Otto Bock HealthCare GmbH, Duderstadt (DE)

( * ) Notice: Subject to any disclaimer, the term of this patent is extended or adjusted under 35 U.S.C. 154(b) by 18 days.

(21) Appl. No.: 12/300,131

(22) PCT Filed: May 8, 2007

(86) PCT No.: PCT/DE2007/000841

§ 371 (c)(1),
(2), (4) Date: Nov. 10, 2008

(87) PCT Pub. No.: WO2007/128299

PCT Pub. Date: Nov. 15, 2007

(65) Prior Publication Data

US 2009/0171468 A1 Jul. 2, 2009

(30) Foreign Application Priority Data

May 9, 2006 (DE) .................. 10 2006 021 802

(51) Int. Cl.
*A61F 2/64* (2006.01)
*A61F 2/68* (2006.01)

(52) U.S. Cl. .......................................... 623/44; 623/43
(58) Field of Classification Search ............. 623/39–46, 623/24–26
See application file for complete search history.

(56) References Cited

U.S. PATENT DOCUMENTS

| 2005/0015156 | A1 | 1/2005 | Hikichi |
| 2005/0283257 | A1* | 12/2005 | Bisbee et al. ................. 623/24 |
| 2006/0293761 | A1* | 12/2006 | Baumann et al. .............. 623/26 |

FOREIGN PATENT DOCUMENTS

| DE | 19859931 | 7/2000 |
| DE | 102004034579 | 2/2005 |
| JP | 2005230207 | 2/2005 |
| WO | 2005087144 | 9/2005 |

OTHER PUBLICATIONS

International Search Report for PCT/DE2007/000841, mailed Apr. 10, 2007, 3 pages.

* cited by examiner

*Primary Examiner*—Bruce E Snow
(74) *Attorney, Agent, or Firm*—Faegre & Benson, LLP

(57) ABSTRACT

The invention relates to the control of a passive prosthetic knee joint with adjustable damping in the direction of flexion such that a prosthetic unit attached to the knee joint can be adapted for climbing stairs.

12 Claims, 2 Drawing Sheets

CONTROL OF A PASSIVE PROSTHETIC KNEE JOINT WITH ADJUSTABLE DAMPING

CROSS-REFERENCE TO RELATED APPLICATION

This patent application is a national stage application of International Application PCT/DE2007/000841, filed on May 8, 2007, which claims priority to German Patent Application No. 10 2006 021802.7, filed on May 9, 2006. The entire contents of both applications are hereby expressly incorporated by reference.

TECHNICAL FIELD

The invention relates to the control of a passive prosthetic knee joint with adjustable damping in the direction of flexion such that a prosthetic unit, with upper attachment elements and with a connection element to an artificial foot, which elements are secured on the prosthetic knee joint, can be adapted for climbing stairs.

BACKGROUND

Prosthesis wearers who require a knee prosthesis have to accept compromises in terms of the damping of the flexion and extension in the configuration of their prosthesis, since passive prosthetic knee joints are optimized only for certain uses, and, therefore, significantly different movement patterns are either not possible or are only possible with extraordinary difficulty. Thus, the movement sequence for walking on level ground, for which most of the passive prosthetic knee joints with flexion and extension damping are designed, requires substantially different damping characteristics than those for climbing stairs. Therefore, with the conventional knee joint prostheses, the prosthesis wearer climbs stairs by a procedure in which, standing in front of the stairs, the healthy leg is lifted onto the first step and the contralateral leg is then pulled up onto this same step. The walking speed may possibly be increased if the healthy leg is placed on every second step, but this is very demanding.

In conventional knee joint prostheses designed for walking on level ground, the necessary low extension damping of the prosthetic knee joint has the effect that, when climbing stairs, an abrupt extension takes place when pushing oneself upward, and this subjects the prosthesis wearer to an unacceptably high load. Balancing of the leg provided with the prosthesis is also not possible, because three joints, namely the ankle joint, the knee joint and the hip, are arranged one above the other and the prosthesis wearer can only directly control the hip joint. Even when lifting the prosthetic foot in order to reach the next step up, the problem arises that the prosthetic foot is moved onto the riser or onto the underside of the next step tip, since the necessary flexion damping in the swing phase control for walking on level ground makes it impossible to reach the top face of the next step up. The flexion drive mechanism provided in active knee joints for the purpose of lifting the foot and the extension drive mechanism for straightening the knee and lifting the body via the leg provided with the prosthesis is very complicated and very heavy. Furthermore, the swing phase control for walking on level ground is very limited in these active prosthetic knee joints.

SUMMARY

An object of the present invention is to make available a control mode for a passive knee joint with which an alternating climbing of stairs is possible for a prosthesis wearer. According to the invention, this object is achieved by a control having the features of claim 1. Advantageous embodiments and developments of the invention are set forth in the dependent claims.

In the control mode according to one embodiment of the invention, a passive prosthetic knee joint with adjustable damping in the direction of flexion allows a prosthetic unit, with an upper element attachable to the knee joint and a connection element to an artificial foot, to be adapted for climbing stairs. First, a low-torque lift of the prosthetic foot is detected. After the detection of a low-torque lift of the prosthetic foot, flexion damping in the lift phase is lowered, specifically to a level below that which is suitable or optimized for walking on level ground. By lowering the flexion resistance during lifting of the prosthetic foot, it is possible to obtain a knee angle that allows the prosthetic foot to be more easily placed on the next step up. More particularly, a flexion of the hip, the low-torque lift of the prosthetic foot, and the mass inertia of the prosthetic foot, results in a passive prosthetic knee joint angle which, by bringing forward the hip or by a corresponding extension through the force of gravity, is sufficient to negotiate the step edge and to position the prosthetic foot over the step. It is advantageous in this case for the weight distribution in the prosthesis to be configured such that the center of gravity is arranged as far as possible in the distal direction, for example in the connection element to the prosthetic foot or in the prosthetic foot itself. To this end, for example, the control unit of the knee system can be arranged distally instead of near the knee such that, without increasing the weight of the prosthesis through extra weights in the prosthetic foot, the desired effect of the knee flexion is achieved with a low-torque lift of the prosthetic foot.

During a subsequent foot placement and hip-straightening phase, the flexion damping and optionally the flexion extension is increased to allow the prosthesis to be straightened. In one embodiment, the flexion damping and possibly the extension damping is increased to a level above a damping for a swing phase control for walking on level ground, such that a controlled extension or straightening of the hip joint, knee joint and of the ankle joint can take place.

After the step edge has been negotiated, the knee is straightened through the force of gravity. To permit positioning of the prosthetic foot located over the step, the flexion damping is increased prior to straightening the prosthetic knee joint, such that the prosthetic foot can be positioned via the hip angle directly controlled by the patient.

In the foot placement phase and, if appropriate, the hip-straightening phase, the flexion damping is preferably increased to a maximum value to reduce or avoid a lowering caused by an insufficient hip-straightening torque. In one embodiment, the flexion damping in the foot placement and hip-straightening phase is maintained until the hip is completely straight.

In one embodiment, extension damping is set during the lift phase, foot placement phase and hip-straightening phase. During the lift phase, extension damping is set to avoid a gravity-induced straightening of the prosthetic knee joint or a dropping of the prosthetic foot. During the foot placement and hip-straightening phase, extension damping is set to position the foot down in a controlled manner. In contrast, if extension damping was completely absent during the hip-straightening phase, this would result in an unnatural upward bounding movement of the patient, which would lead to a stop and an abrupt interruption in maximum extension of the knee joint. In open steps, that is to say without risers, a lifting of the prosthetic foot without extension damping can have the effect that the prosthetic foot is pushed under the next step up.

The flexion damping is preferably increased as a function of the change of the knee angle. As soon as a defined knee angle is reached, which is generally greater than a knee angle suitable for walking on level ground in a swing phase control, the flexion damping is increased. Alternatively or in addition, the flexion damping can be increased or lowered as a function of the axial force acting on the lower leg shaft. If the axial force drops sufficiently quickly to approximately zero with the knee almost straightened, this is an indicator for initiation of a stair-climbing mode.

In addition or alternatively to this, the vertical acceleration of the leg, that is to say the thigh or lower leg and hip, can take place with a simultaneous drop in axial force from triggering for activation of a corresponding flexion damping control and extension damping control for climbing stairs. Moreover, a sufficiently rapid bending of the hip can cause the knee to bend with little or no axial force. Instead of an axial force, knee-straightening torque, ankle torque or a combination of the forces and torques can be detected to initiate the stair-climbing mode.

The detection of a low-torque lift can be achieved mechanically via a caliper or via a force or torque sensor. The caliper can be designed, for example, as a slide which is mounted in a guide and which, with almost perpendicular lifting of the prosthetic foot, moves into a switching position that reduces the flexion damping. The measurement of the forces or torques can be achieved by known sensor devices. Alternatively, the low-torque lift can take place via a measurement of the horizontal acceleration of the prosthetic foot and the detection of a bending in the knee joint. In contrast to walking on level ground, a low horizontal acceleration of the prosthetic foot, that is to say with almost perpendicular lifting, causes a high bending to take place in the prosthetic knee joint, which indicates stair-climbing. Moreover, the torque at the front of the prosthetic foot can be detected to determine whether the prosthesis user would like to move in a horizontal direction during walking resulting in a very high loading of the front of the prosthetic foot, or whether there is a reduced axial force and a flexion in the knee joint with the prosthetic foot set down.

To achieve the necessary flexion for negotiating the step height after the lift, a flexion support in the lift phase can be achieved via a pretensioned spring or another force-storing mechanism. Likewise, free extension can be supported by a spring when a certain time has elapsed after lowering the flexion damping. This is necessary for safety reasons, to prevent unwanted damping control in the event of erroneous triggering of the stair-climbing mode.

The increase of the flexion damping and if appropriate of the extension damping is initiated when the prosthetic foot, after being lifted, is placed down again, for example if an increase of the axial force is determined. Alternatively, with the knee angle remaining more or less constant, the extension and flexion damping can be increased.

The flexion damping in the lift phase can be lowered to a minimum value, such that the damping effective in each system is not further increased on account of friction.

The detection both of the low-torque or torque-free lift and also of the lowering of the flexion damping can be done mechanically, and similarly the changing of the various damping, in order to permit a prosthesis construction that is as simple as possible.

BRIEF DESCRIPTION OF THE DRAWINGS

An illustrative embodiment is explained in more detail below with reference to the figures.

DETAILED DESCRIPTION

Figure 1:
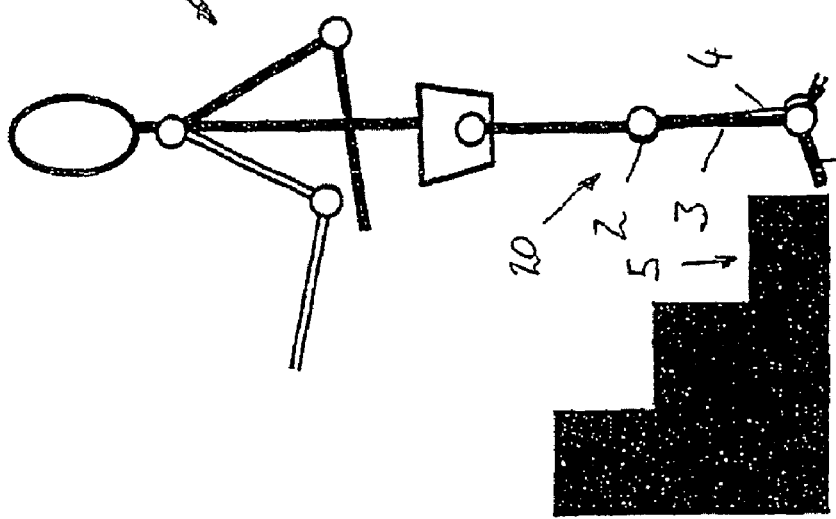

FIG. 1 shows a prosthesis wearer 1 with a knee joint prosthesis 2 which is secured by upper attachment elements to a femoral stump. The prosthetic leg 20 stands with the healthy contralateral leg 4 in front of a step.

Figure 2:
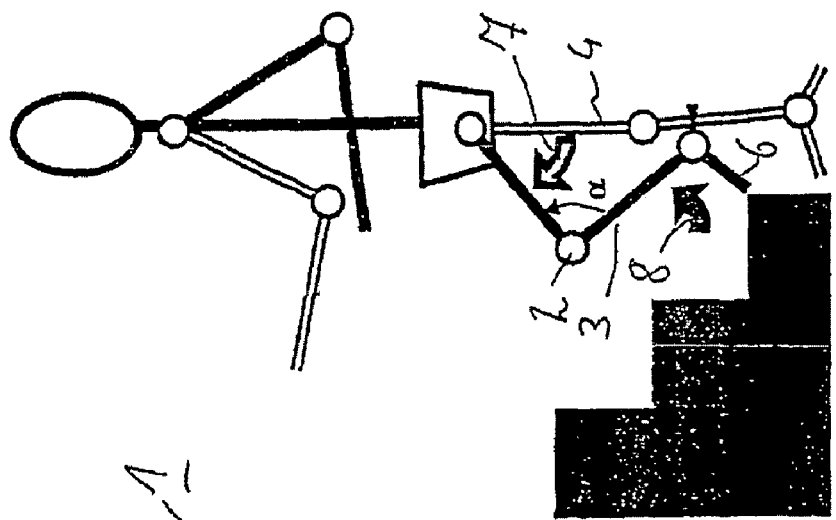

To reach the next step up, a prosthetic foot 6 has to be guided over the step edge. An active bending of the hip, as is indicated by the arrow 7, assists the passive bending of the knee, which is shown by the arrow 8 and which, because of the mass inertia both of the prosthetic foot 6 and also of the connection element 3, occurs from the prosthetic knee joint 2 to the prosthetic foot 6. For this purpose, a minimum extension damping is required to ensure that, after a flexion of the hip, the prosthetic foot 6 does not swing forward and is not moved against the riser or under the step 5. In the lift phase, as shown in FIG. 2, the prosthetic foot 6 is guided upward, as far as possible in a perpendicular manner, this possibly being initiated by a slight rearward movement. The lift is detected via the flexion angle $\alpha$ between the connection element 3 and the thigh or via a reduction of the axial force in the connection element 3, without flexion of the prosthetic foot 6. It is also possible to detect the stair-climbing mode, and thus the lowering of the flexion damping to a value below the normal swing phase control, preferably to the minimum value, via a horizontal rearward movement of the prosthetic foot 6 in conjunction with a bending of the hip.

Figure 3:
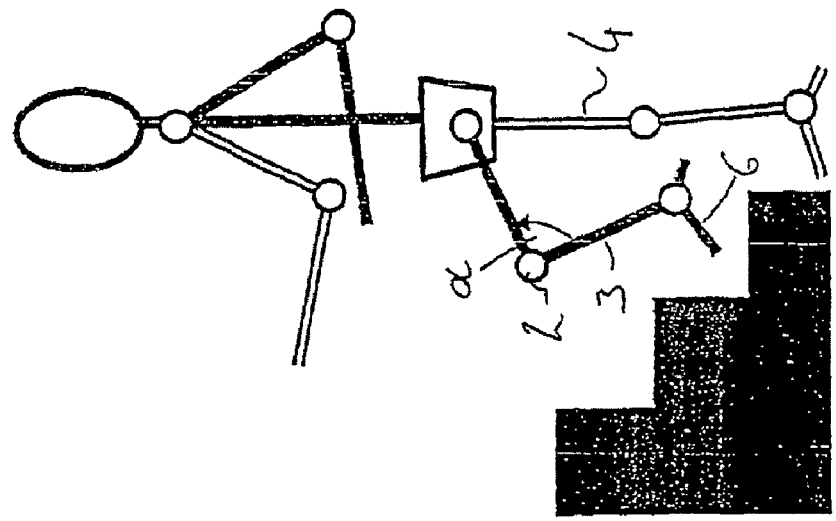
FIGS. 1 to 6 are schematic depictions showing the sequence involved in alternating stair-climbing with a passive knee joint prosthesis.

After the step edge has been negotiated and the lift phase completed, as is shown in FIG. 2, a secure positioning of the prosthetic foot 6 on the step is required. For this purpose, the prosthetic foot 6 has to be moved forward, which can be achieved by extension as a result of the force of gravity. For this purpose, an extension damping can be reduced, if this has not already been done in the lift phase. A prosthetic knee joint 2 that is sufficiently damped in flexion and extension prior to straightening allows the prosthesis wearer 1 to position the prosthetic foot 6, by changing the hip angle. In the lowering and hip-straightening phase, the flexion and extension are preferably strongly damped to control the foot placement, and to prevent a spontaneous backward fall in the event that the hip-straightening torque is insufficient. The extension remains damped so as to be able to control the speed of straightening of the hip and knee. This is shown in FIG. 3.

Figure 4:
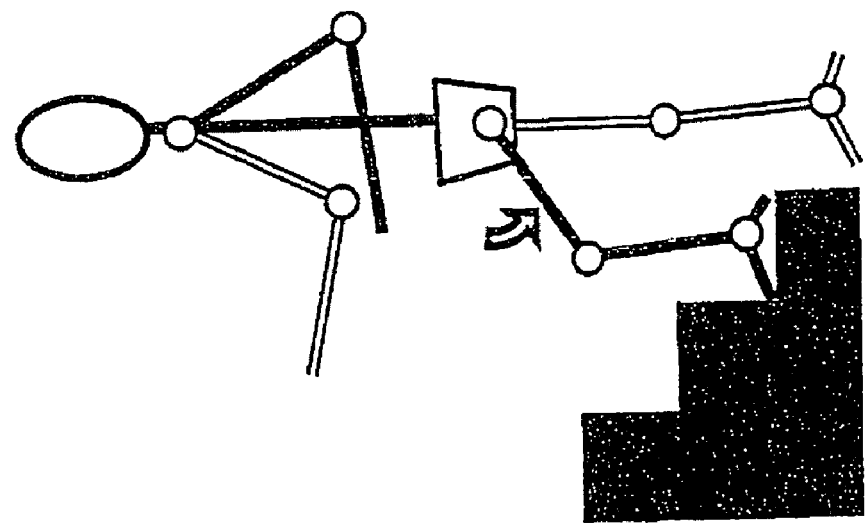

In FIG. 4, the foot placement phase is completed. The prosthesis wearer 1 can initiate straightening of the knee with a hip-straightening torque. The straightening of the knee can be assisted by an extension of the healthy foot.

Figure 5:
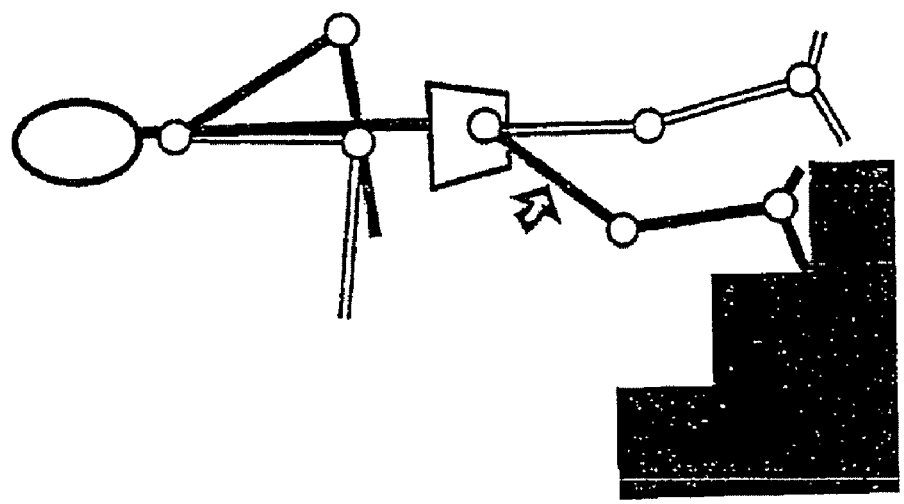

FIG. 5 shows the increasing straightening of the knee through application of a hip torque. The increasing straightening of the knee shortens the effective lever and facilitates the straightening of the knee through the straightening of the hip.

Figure 6:
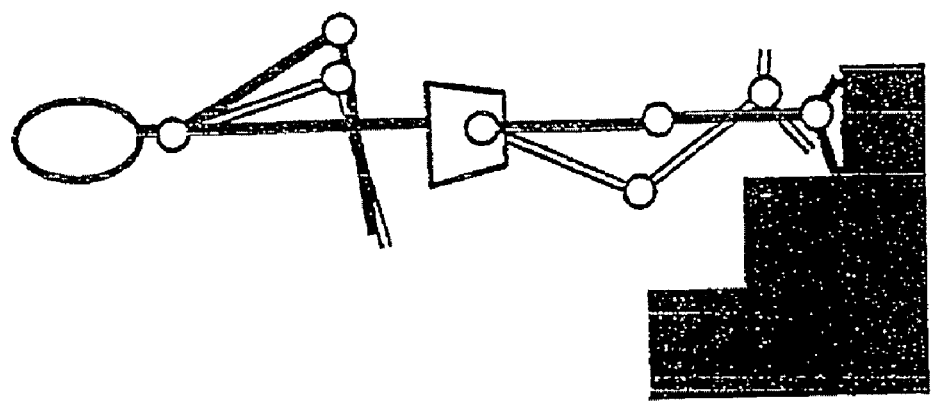

FIG. 6 shows the complete extension of the leg provided with the knee joint prosthesis 2. The contralateral leg 4 is moved past the prosthetic leg 20 and placed on the next step up, such that alternating climbing of stairs is possible with the passive knee joint prosthesis.

Accordingly, the control is configured in such a way that, during the lift of the prosthetic foot 6 a flexion resistance is set that results in a knee angle α, which allows the prosthetic foot 6 to be placed on the next step. Flexion support by spring mechanisms may facilitate the lifting movement and make it easier to negotiate the step height.

If no action is to take place after the stair-climbing mode has been triggered by detection of a low-torque lift, a free extension is set, said free extension being set in a time-dependent manner. The time function can also be mechanical. The low-torque lift can be detected via the mass inertia, if the healthy leg is first set down and only the second step is intended to be negotiated by the leg provided with the prosthesis. If the prosthetic foot is first unloaded and the prosthetic knee joint then bent, the stair-climbing mode is set. Damping both in the direction of extension and also in the direction of flexion after the lift phase, that is to say during the hip-straightening phase, is maintained until a complete extension of the prosthetic knee joint is reached or detected.

The invention claimed is:

1. A method for initiating and implementing a stair-climbing mode in a passive prosthetic knee joint connected to a prosthetic leg unit including a prosthetic foot comprising:
   detecting a low-torque lift of the prosthetic foot;
   initiating a lift phase, in which a flexion damping level of the knee joint is reduced to a level below that which is used for walking on level ground;
   detecting a placement of the prosthetic foot; and
   initiating a lowering phase, in which the flexion damping level is increased to a level above that which is used for walking on level ground.

2. The method of claim 1, wherein in the lowering phase, an extension damping level is increased to a level above that which is used for walking on level ground.

3. The method of claim 2, wherein the flexion damping are increased to maximum levels in the lowering phase.

4. The method of claim 1, wherein the flexion damping is reduced to a minimum level in the lift phase.

5. The method of claim 1 further comprising the step of, during the lowering phase, maintaining the flexion damping level until a straightened hip is detected.

6. The method of claim 1, further comprising the step of, during the lowering phase, detecting a knee angle and establishing the flexion damping level as a function of the detected knee angle.

7. The method of claim 1 wherein at least one of the detecting steps comprises the step of detecting an axial force along the prosthetic unit.

8. The method of claim 1 wherein an extension damping level is established during each of the lifting and lowering phases.

9. The method of claim 1 wherein the step of detecting the low torque lift comprises measuring a horizontal acceleration of the prosthetic foot and by detecting a bend in the knee joint.

10. The method of claim 1 wherein the step of detecting the low torque lift comprises detecting a torque at the front of the prosthetic foot.

11. The method of claim 1 wherein the step of detecting the placement of the foot comprises measuring an axial force measurement along the prosthetic unit.

12. The method of claim 1 wherein after initiating the lifting phase, a time controlled free extension is set.

* * * * *